United States Patent
Hopper

(10) Patent No.: US 7,905,233 B2
(45) Date of Patent: Mar. 15, 2011

(54) PATIENT RESTRAINT

(75) Inventor: Christopher J. Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 348 days.

(21) Appl. No.: 12/101,774

(22) Filed: Apr. 11, 2008

(65) Prior Publication Data

US 2008/0251088 A1   Oct. 16, 2008

Related U.S. Application Data

(60) Provisional application No. 60/923,137, filed on Apr. 12, 2007.

(51) Int. Cl.
*A61B 19/00* (2006.01)
*B65H 23/04* (2006.01)
*A63H 17/36* (2006.01)

(52) U.S. Cl. ............... 128/869; 242/396; 464/184

(58) Field of Classification Search ............ 128/869, 128/876, 878; 297/474, 475, 483; 5/600, 5/621, 623, 624, 628, 630, 650, 647; 242/396.1, 242/396.2, 396.3, 396.4; 464/184
See application file for complete search history.

(56) References Cited

U.S. PATENT DOCUMENTS

| | | |
|---|---|---|
| 2,181,141 A | 11/1939 | Lovegran |
| 3,729,102 A | 4/1973 | Shumaker |
| 3,877,655 A | 4/1975 | Cardinal et al. |
| 4,307,853 A | 12/1981 | Higbee et al. |
| 4,967,976 A | 11/1990 | Kawai et al. |
| 4,974,876 A | 12/1990 | Svensson et al. |
| 5,236,144 A | 8/1993 | Kautz |
| 5,289,624 A | 3/1994 | Wagner, Jr. et al. |
| 5,492,285 A | 2/1996 | Hamrick |
| 5,735,478 A * | 4/1998 | Malinow et al. ........... 242/376.1 |
| 5,911,378 A | 6/1999 | Plestan |
| 6,286,779 B1 | 9/2001 | Devine |
| 6,398,149 B1 | 6/2002 | Hines et al. |
| 6,568,621 B2 | 5/2003 | Hiramatsu et al. |
| 6,575,498 B2 | 6/2003 | Nagata et al. |
| 6,874,632 B2 | 4/2005 | Thiessen |
| 7,128,291 B1 | 10/2006 | Schanke et al. |
| 2004/0221388 A1* | 11/2004 | Votel ........................... 5/81.1 HS |

* cited by examiner

*Primary Examiner* — Kevin C Sirmons
*Assistant Examiner* — Ophelia Hawthorne
(74) *Attorney, Agent, or Firm* — Van Dyke, Gardner, Linn & Burkhart, LLP

(57) ABSTRACT

A patient support incorporates a patient retention device includes frame, a rotatable shaft, a torque-producing device, and a flexible restraint member. The shaft has a cantilevered portion that extends from the frame and windably receives the flexible restraint member at the cantilevered portion. Optionally, a winding member is releasably coupled to the cantilevered portion of the shaft for receiving the flexible restraint member. The winding member is non-rotatable relative to the shaft, and is readily removable and replaceable. The torque-producing device applies a torque to the shaft to wind the flexible restraint member onto the shaft or winding member.

20 Claims, 4 Drawing Sheets

PATIENT RESTRAINT

CROSS REFERENCE TO RELATED APPLICATION

The present application claims the benefit of U.S. provisional application Ser. No. 60/923,137, filed Apr. 12, 2007, which is hereby incorporated herein by reference in its entirety.

FIELD OF THE INVENTION

The present invention relates in general to the field of restraint devices. In particular, the invention relates to patient restraint devices on hospital-type stretchers, chairs, and/or beds and/or pre-hospital chairs and cots.

SUMMARY OF THE INVENTION

The present invention provides a patient retention device that is configured to restrain a patient to a patient support surface, such as a stretcher, a bed, a chair, a cot, or the like. The patient retention device is operable to allow a caregiver to pull a flexible restraining member across a patient to restrain the patient on a stretcher, for example, such as while the stretcher is moving or when the patient is otherwise at risk of exiting the stretcher unsafely.

According to one form of the present invention, a patient retention device includes a rotatable shaft, a torque-producing device operatively connected to the shaft to rotate the shaft about an axis of rotation, and a flexible restraint member coupled to the shaft outboard of the torque-producing device. The flexible restraint member is selectively windable and unwindable from the shaft.

According to another form of the present invention, a patient retention device includes a frame, a shaft, a flexible restraint member, a winding member, and a torque-producing device. The shaft is rotatably mounted to the frame and has a cantilevered portion extending from the frame. The winding member is at the cantilevered portion of the shaft and is adapted to receive the flexible restraint member. The winding member is non-rotatable relative to the shaft. The torque-producing device is operatively connected to the shaft.

According to still another form of the present invention, a patient retention device includes a winding member having a first end and a second end, a rotatable shaft having a first end and a second end, a torque-producing device, and a flexible restraint member. The second end of the shaft is adapted to receive, and may be adapted to releasably receive, the first end of the winding member. The torque-producing device is operatively connected to the shaft to rotate the shaft about an axis of rotation. The flexible restraint member is attached to the winding member such that the winding member is cantilevered from the second end of the shaft.

In one aspect pertaining to any of the above forms of the present invention, the patient retention device further comprises a lock mechanism arranged at the shaft to selectively prevent rotation of the shaft. In another aspect, the winding member is adapted to releasably receive the flexible restraint member. In yet another aspect, the patient retention device further comprises a cover disposed over the torque-producing device and a portion of the shaft. In still another aspect pertaining to any of the above forms of the present invention, the patient retention device is used in combination with a patient stretcher, a patient cot, a patient bed, or a chair.

According to another form of the invention, a method of mounting a flexible restraint member on a patient retention device includes providing a retractor assembly having a rotatable shaft and a torque-producing device operatively connected to the shaft to rotate the shaft about an axis of rotation; and removably mounting a flexible restraint member to the shaft outboard of the torque-producing device.

In one aspect, the method further includes providing a replacement flexible restraint member, removing the flexible restraint member from the shaft, and placing the replacement flexible restraint member onto the shaft.

According to another form of the invention, a method of mounting a flexible restraint member on a patient retention device includes providing a frame, a shaft rotatably mounted to the frame and having a cantilevered portion removably mounting a flexible restraint member extending from the frame, and a torque-producing device operatively connected to the shaft to rotate the shaft about an axis of rotation. Next, the flexible restraint member is wound about the shaft. Then, the flexible restraint member is pulled to unwind the flexible restraint member from the shaft.

In one aspect, the method further includes providing a replacement winding member and a replacement flexible restraint member, removing the winding member from the shaft by pulling the winding member in an axial direction, and placing the replacement winding member and the replacement flexible restraint member onto the shaft at the cantilevered portion.

These and other objects, advantages, purposes, and features of the present invention will become apparent upon review of the following specification in conjunction with the drawings.

DESCRIPTION OF THE PREFERRED EMBODIMENTS

The present invention is directed to a retention device, and more specifically, a retention device having a flexible restraint member for restraining a patient lying on a cot, a stretcher, or a bed, or sitting in a chair, including a stair chair. The retention device incorporates a retractor mechanism and an external winding assembly for windably receiving the flexible restraint member. The retention device assists caregivers in securing a patient to a cot, stretcher, bed, or chair, and improves reliability and cleanability by providing a removable flexible restraint member that may be removed for cleaning or replacement. In addition, the winding assembly may accommodate a range of flexible restraint members so that when one flexible restraint member is removed, it can be replaced with another flexible restraint member having a different width and/or material, which allows the retention device to be customized for various patients and applications. Further, the risk of exposing the retractor mechanism to debris and bodily fluids is reduced, and direct access to the external winding assembly is provided for cleaning and/or for replacing at least a portion of the external winding assembly.

Figure 1:
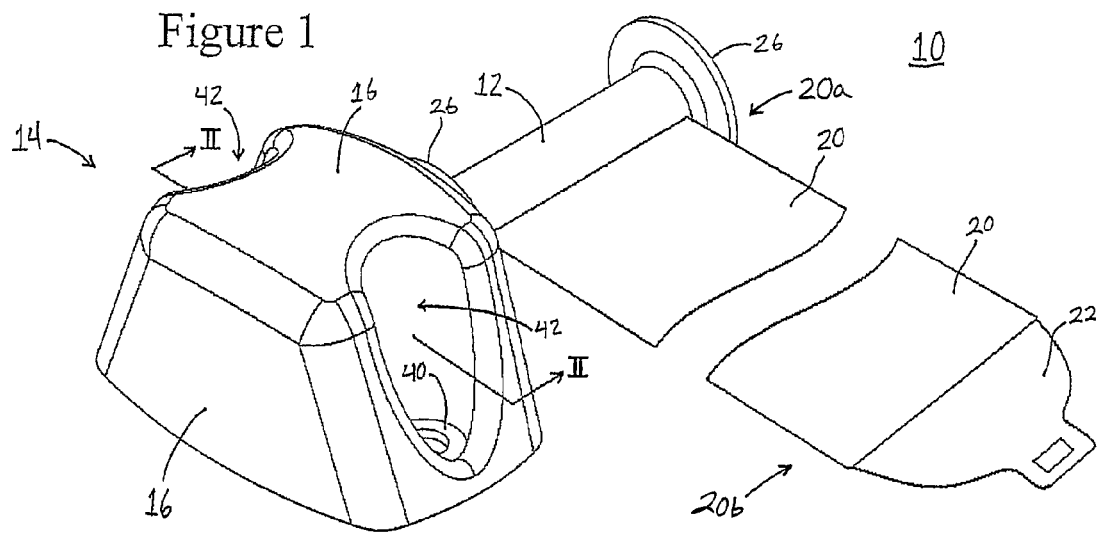
FIG. 1 is a perspective view of a restraining device of the present invention.

Referring now to FIG. 1, the numeral 10 designates a retention device that incorporates a rotatable winding element 12 that is substantially external to a retractor assembly 14. A housing 16 substantially covers retractor assembly 14 to protect retractor assembly 14 from contaminants. Winding element 12 may be incorporated into a shaft 18 (FIGS. 2, 4, and 6), or is a separate element connected to retractor assembly 14 via shaft 18 as in the illustrated embodiment, and as will be described in greater detail below.

A flexible restraint member 20 is attached to and selectively windable upon winding element 12. Flexible restraint member 20 may be a length of woven fabric webbing of a type commonly used for vehicular seat belts, for example, or may be a strap, cabling material such as a cable, a rope, a cord, or the like, or any suitably strong and flexible member for restraining a patient on a cot, such as an ambulance cot, a stretcher, a bed, or a chair, while remaining windable upon winding element 12. A proximal end 20a of flexible restraint member 20 may incorporate an attachment feature to facilitate its attachment to, and removal from, winding element 12. The attachment feature may comprise, for example, an end having increased thickness, a loop, apertures for receiving fasteners, or the like. A distal end 20b of flexible restraint member 20 may incorporate an attachment feature such as a tongue 22 (FIG. 1) adapted to be received in a releasable coupler or buckle (not shown) located opposite retention device 10 on the stretcher, bed, cot, or chair.

Flexible restraint member 20 may be made of nylon or polyester webbing, for example, or any suitably strong and flexible material that resists degradation in the presence of water, bodily fluids, or other chemicals commonly present in a patient care environment, and may be disposable and/or readily cleanable. Flexible restraint member 20 may incorporate padding, or may have padding installed thereon when flexible restraint member 20 is drawn from winding element 12. Additionally, flexible restraint member 20 may be relatively wide, such as four or six or eight inches or more, such as for bariatric patients, or may be relatively narrow in width, such as one inch or less, such as for infants or small patients.

Winding element 12 is removably disposed about a distal end 18a (FIGS. 4 and 6) of shaft 18 and is non-rotatable relative to shaft 18. Winding element 12 has an axial aperture or passageway 23 (FIG. 6) for receiving shaft 18, the passageway 23 having substantially the same cross section as shaft 18, such as a constant semi-circular cross section with flat sides (a "double-D" section). Winding element 12 windably receives flexible restraint member 20 to selectively either unwind and pay out flexible restraint member 20, or wind and take up flexible restraint member 20. Winding element 12 has a length that is approximately equal to or greater than the width of flexible restraint member 20. Winding element 12 is connected to proximal end 20a of flexible restraint member 20 at an aperture 24 (FIG. 5) configured for releasably receiving flexible restraint member 20 in an outer surface of winding element 12 with a friction or interference fit. Alternatively, fasteners such as screws, bolts, rivets, adhesive, or the like may be used to releasably fix flexible restraint member 20 to winding element 12.

Winding element 12 may optionally incorporate a flange 26 at one or both ends of winding element 12. Flanges 26 have a diameter greater than the outer diameter of winding element 12 and are adapted to prevent flexible restraint member 20 from being displaced off of winding element 12 as flexible restraint member 20 is wound onto, or unwound from, winding element 12. Winding element 12 may farther incorporate a radial ridge or a bump at the inner surface of its axial aperture, the ridge or bump being received by a radial groove or an indentation in shaft 18 when winding element 12 is fully installed on shaft 18.

The ridge and groove engage to provide a positive indication (e.g. a "snap") when winding element 12 is properly installed on shaft 18 and/or the ridge and groove engage to releasably retain winding element 12 on shaft 18. Winding element 12 and flanges 26 may be made from a polymer or a metal, for example, or any suitably strong material that resists corrosion or deterioration in the presence of water, bodily fluids, or other chemicals commonly present in a patient care environment, and may be disposable and/or readily cleanable.

Although shown in the illustrative embodiment as being a separate feature, those skilled in the art will appreciate that a winding element may be incorporated into a shaft without departing from the scope of the invention. In such an alternative embodiment, the shaft has a cantilever portion with optional flanges to retain flexible restraint member 20 thereon. Such a shaft may incorporate an attachment feature such as an elongated slot through the shaft for receiving flexible restraint member 20, threaded holes for receiving threaded fasteners that are driven through the flexible restraint member to fasten it to the shaft, a closeable clamp feature for clamping the proximal end 20a of flexible restraint member 20, or any other feature for connecting a flexible restraint member to a shaft. In such an embodiment, flexible restraint member 20 is removably attached directly to the shaft.

In another alternative embodiment, a shaft may have a distal end proximate an outer surface of a retractor assembly, the distal end incorporating an attachment feature. A winding element is removably attachable to the shaft in cantilever fashion such that the winding element and shaft rotate together when they are mated. In still another alternative embodiment, a winding element has a shaft portion and a winding portion. The shaft portion is insertable into a retractor assembly, and is releasably locked therein, while the winding portion is cantilevered out from the retractor assembly.

Figure 4:
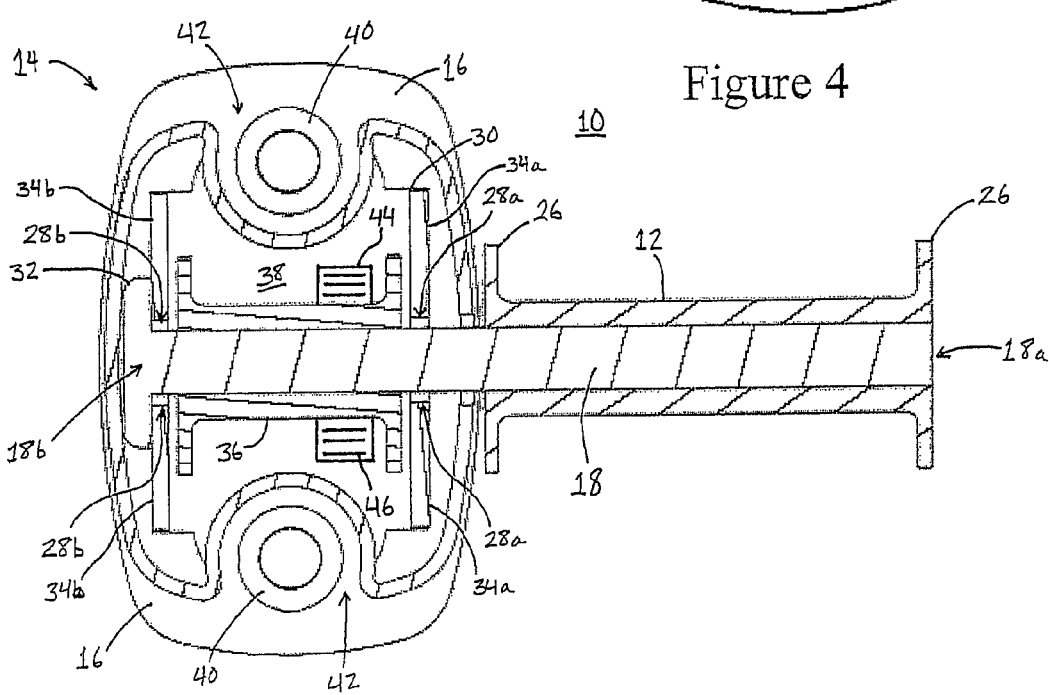
FIG. 4 is a cross-sectional view of the restraining device taken along section IV in FIG. 3.
Figure 5:
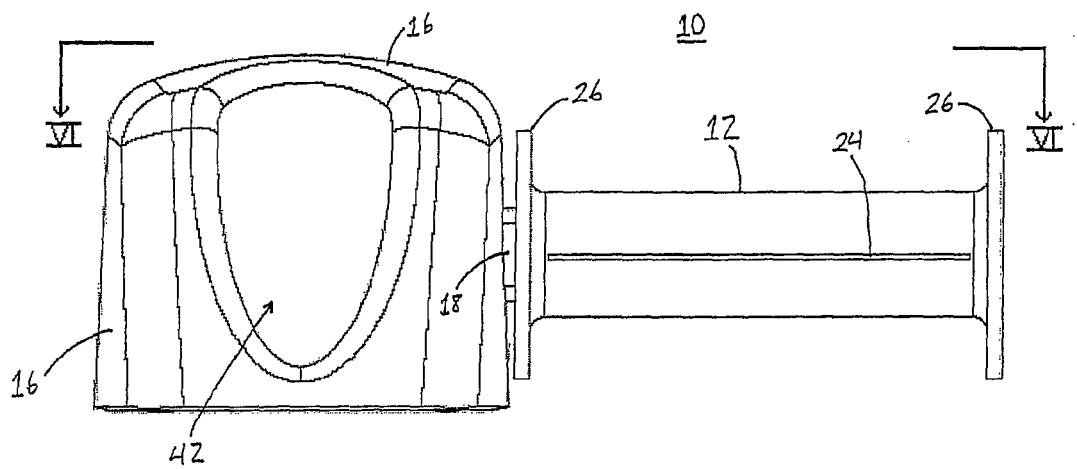
FIG. 5 is a front view of the restraining device.
Figure 6:
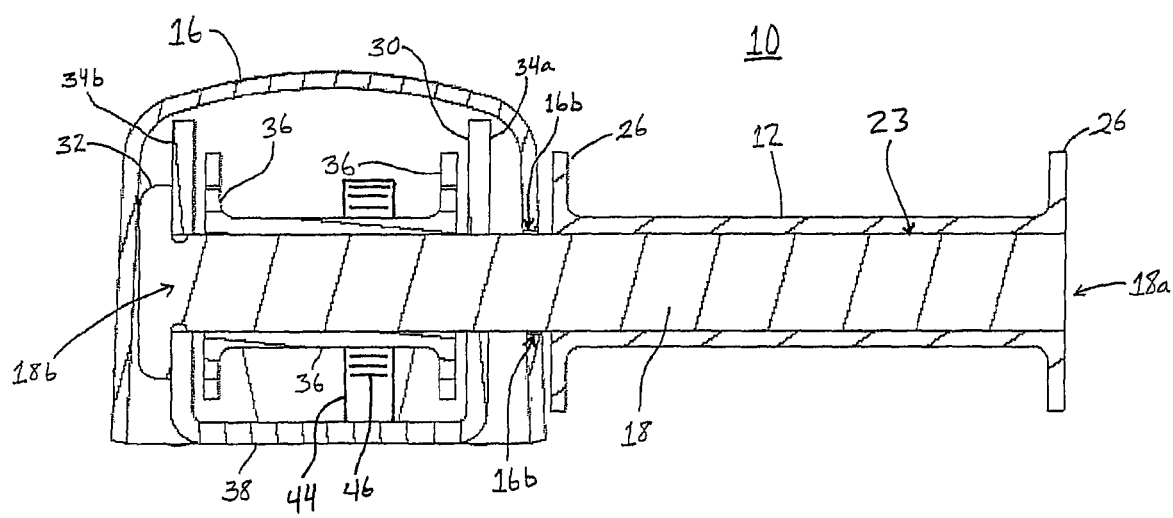
FIG. 6 is a front sectional view of the restraining device taken along section VI in FIG. 5.

Shaft 18 is an elongated member that is partially retained within retractor assembly 14, and is rotatably mounted thereto, such as is shown in FIGS. 4 and 6. Shaft 18 has a cantilever portion near distal end 18a, and a rotatably mounted portion near a proximal end 18b. Shaft 18 is non-circular in cross section, and may have a double-D section such as that shown in FIG. 6. Shaft 18 has a diameter less than the diameter of apertures 28a, 28b in a frame 30 of retractor assembly 14, through which shaft 18 is received. Shaft 18 protrudes from a side of retractor assembly 14 such that distal end 18a is located outside retractor assembly 14. Shaft 18 incorporates a flange 32 at proximal end 18b for retaining shaft 18 in retractor assembly 14. Flange 32 is wider than aperture 28b in an upper portion 34b of frame 30, and is located outboard of upper portion 34b. Shaft 18 is adapted to receive a lock mechanism 36 and winding element 12, with lock mechanism 36 disposed toward proximal end 18b and winding element 12 disposed toward distal end 18a. The non-circular cross section of shaft 18 facilitates the connection of both lock mechanism 36 and winding element 12 to shaft 18 such that neither lock mechanism 36 nor winding element 12 is rotatable on shaft 18. Shaft 18 may be made of steel, for example, or any material that is suitably strong and resistant to corrosion.

It will be appreciated by those skilled in the art that although shaft 18 is described as being of substantially constant double-D cross section, shaft 18 may have any non-circular cross section including, but not limited to, triangular section, square section, or substantially any polygon section, for example. It will further be appreciated that shaft 18 may, alternatively, have a generally circular cross section, such as a circular cross section with a splined outer surface, and/or may be of non-constant cross section. For example, shaft 18 may comprise a circular cross section at a proximal end 18b, to which lock mechanism 36 is welded or otherwise rigidly fastened, and a non-circular cross section near distal end 18a, to which winding element 12 is slidably connected.

Optionally, shaft 18 may be rotatably connected to frame 30 via bushings or bearings disposed between shaft 18 and apertures 28a, 28b to prevent or reduce wear of shaft 18 and upper frame portions 34a, 34b at apertures 28a, 28b. Furthermore, a seal may be disposed between shaft 18 and upper frame portion 34a, about aperture 28a, to prevent or substantially reduce contaminants entering retractor assembly 14.

In the illustrated embodiment, retractor assembly 14 comprises frame 30 having a base portion 38 and upper portions 34a, 34b, lock mechanism 36, housing 16, fasteners 40, and shaft 18, as best seen in FIGS. 4 and 6. Frame 30, including base portion 38 and upper portions 34a, 34b, is of single-piece construction, and is configured to be mounted at base portion 38 to a mounting surface. Base portion 38 has two apertures 38a (FIG. 2) for receiving fasteners 40. Upper portions 34a, 34b are substantially parallel to one another and oriented at right angles to base portion 38 such that frame 30 is substantially U-shaped (FIG. 6). Upper portions 34a, 34b each have a respective aperture 28a, 28b adapted to receive shaft 18 such that the shaft's longitudinal axis is substantially parallel to base portion 38 of frame 30. Frame 30 may be made of steel or any material that is suitably strong and resistant to corrosion, and may, for example, be stamped and formed from a single flat metal plate.

Housing 16 substantially covers retractor assembly 14 to protect retractor assembly 14 from contaminants such as debris, bodily fluids, and other chemicals that are commonly found in a patient care environment. Housing 16 has recesses or depressions 42 to allow access to fasteners 40. An aperture 16a (FIG. 2) is located at the bottom of each depression 42 and substantially aligned with each aperture 38a in base portion 38 of frame 30 when housing 16 is installed over retractor assembly 14. Upper portions of fasteners 40 remain exposed above housing 16 and base portion 38, while lower portions of fasteners 40 extend through the apertures and into a mounting surface. Housing 16 has an aperture 16b for receiving shaft 18 (FIGS. 3, 4, and 6) and is open at the bottom such that a bottom edge of housing 16 is generally adjacent and/or in contact with base portion 38 of frame 30.

It will be appreciated by those skilled in the art that housing 16 may optionally incorporate a bottom surface that at least partially encloses a bottom surface of base portion 38, and may fully enclose the bottom surface of base portion 38 such that the entire retractor assembly 14 is substantially isolated from the environment. Housing 16 may be made of a semi-rigid, resilient, and cleanable material such as rubber or polymer, for example, or any suitable material that is sufficiently flexible to facilitate assembly and which is resistant to fluids and chemicals commonly found in a patient care environment. Alternatively, housing 16 may be made of rigid material such as steel, aluminum, alloy, or composite, that is sufficiently strong and resistant to such fluids and chemicals, and is readily cleanable.

As will be appreciated by those skilled in the art, retractor assembly 14 further incorporates a torque device 44 connected to shaft 18 and/or lock mechanism 36. Torque device 44 may, for example, comprise a coil spring 46 having a first end connected either directly or indirectly to frame 30 and a second end connected to shaft 18 or lock mechanism 36. Alternatively, the torque device may comprise an electric motor having an output shaft connected directly to shaft 18, or connected to shaft 18 via a transmission device. Torque device 44 is operable to constantly or intermittently apply torque to shaft 18 so that shaft 18 turns about its longitudinal axis to wind a flexible restraint member 20 about winding element 12 at distal end 18a of shaft 18.

Figure 2:
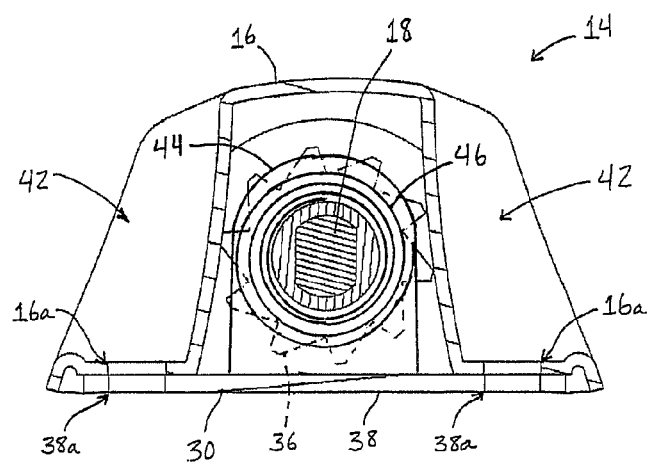
FIG. 2 is a cross-sectional view of the restraining device of FIG. 1 taken along section II in FIG. 1.
Figure 3:
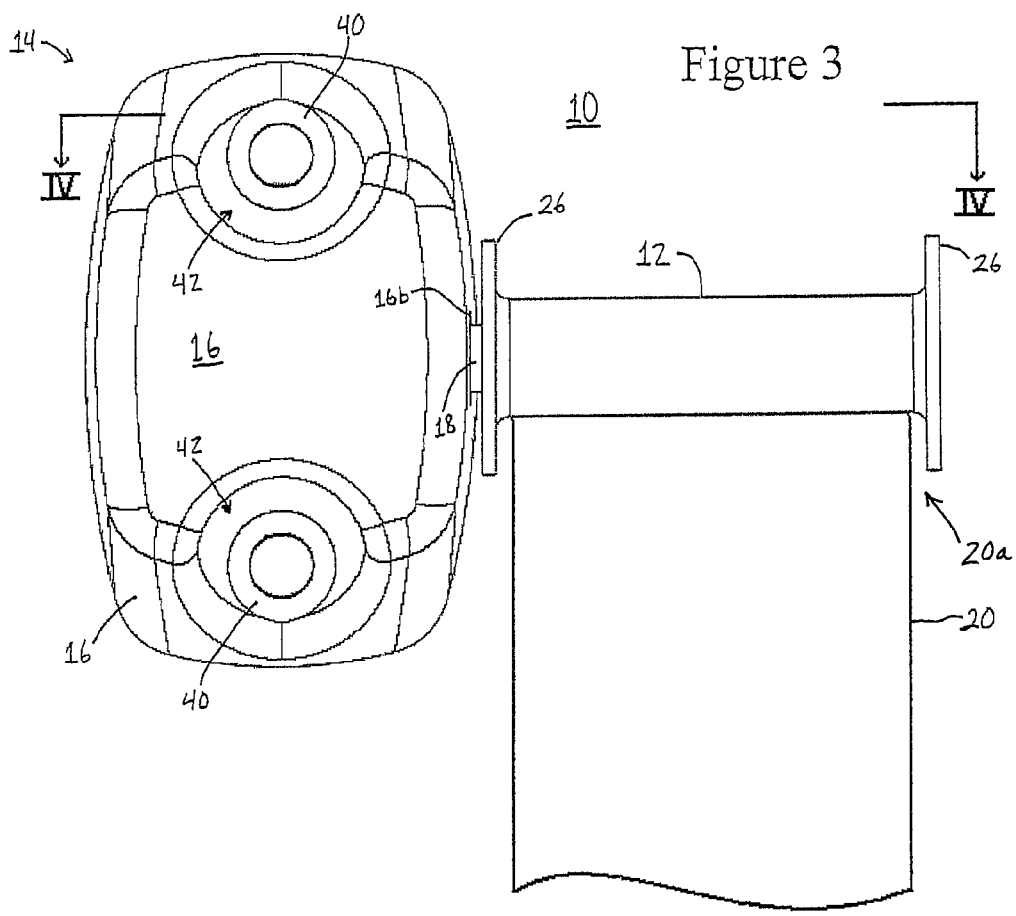
FIG. 3 is a top plan view of the restraining device.

Lock mechanism 36 represents any clutch or manual or automatic locking feature commonly used on retractor mechanisms such as vehicular seat belt retractors. Lock mechanism 36 is mounted on shaft 18 such that lock mechanism 36 and shaft 18 are non-rotatable relative to one another (FIG. 2). Lock mechanism 36 has an axial aperture for receiving shaft 18, the aperture having substantially the same cross section as shaft 18, such as a double-D section, such as is shown in FIG. 2. Lock mechanism 36 may comprise an inertial lock, an electronic sensing lock, a manual lock, or the like. Alternatively, retractor assembly 14 may omit lock mechanism 36, such that shaft 18 is freely rotatable in either direction.

Figure 7:
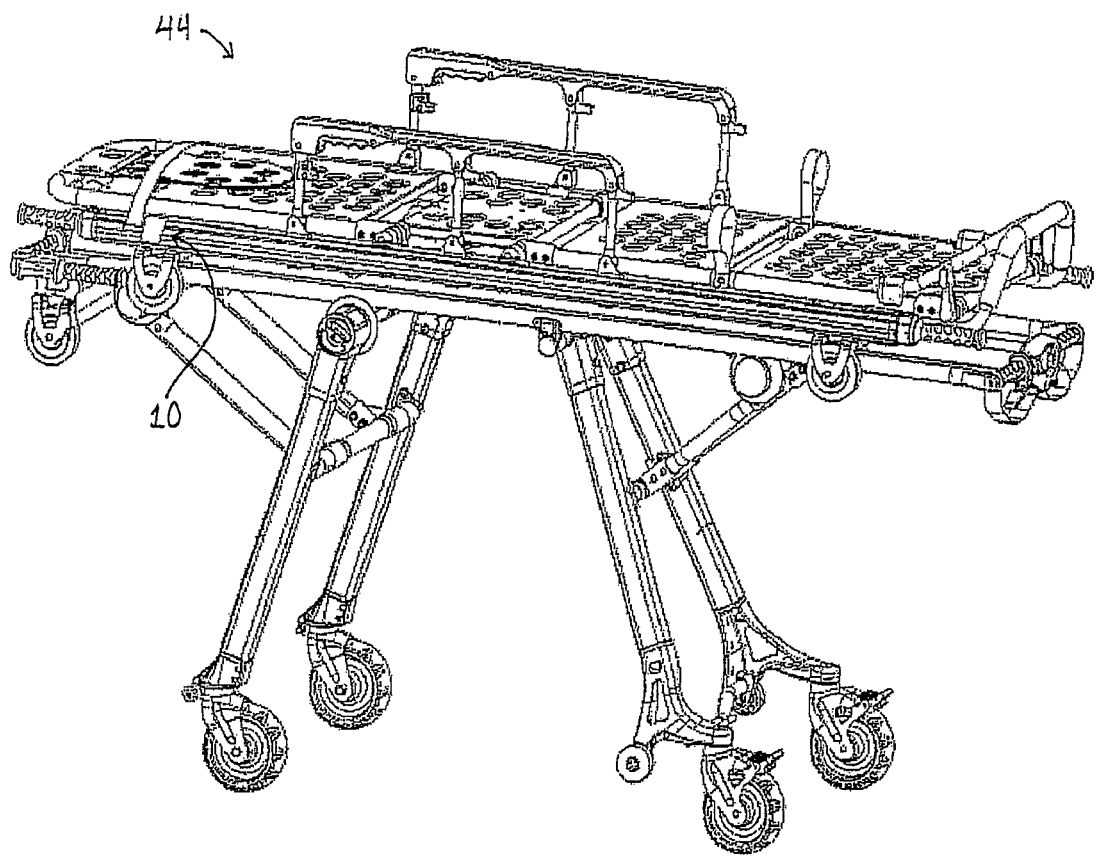
FIG. 7 is a perspective view of a stretcher with the present invention mounted thereon.

Accordingly, retention device 10 may be installed at one side of a patient support such as a cot, a bed, a chair, or a stretcher 44 to facilitate the use of a flexible restraint member 20 over a patient lying upon stretcher 44 (FIG. 7). Initially, a substantial portion of flexible restraint member 20 is wound upon winding element 12. A caregiver grasps the distal end 20b of flexible restraint member 20 and pulls the member 20 across the patient, fastening the member 20 at the opposite side of the bed, the cot, the chair, or the stretcher 44. Torque device 44 applies torque to shaft 18, which transmits torque to winding element 12, which imparts tension to flexible restraint member 20. Optionally, lock mechanism 36 is actuated, or automatically actuates to substantially prevent shaft 18 from paying out an additional length of flexible restraint member 20 while the member 20 is fastened at the side of the cot, the bed, the chair, or the stretcher 44, opposite the retention device 10.

The caregiver may then unfasten flexible restraint member 20 from the side of stretcher 44 opposite the retention device 10, such as by unbuckling tongue 22 and allowing winding element 12 to turn in response to torque transmitted from torque device 44 until substantially all of flexible restraint member 20 is wound upon winding element 12.

To replace a winding element 12 and flexible restraint member 20, element 12 and/or member 20 are grasped and pulled away from retractor assembly 14 until element 12 has been fully removed from shaft 18. Winding element 12 and flexible restraint member 20 may then be cleaned or disposed of, and shaft 18 may be cleaned. A replacement winding element and flexible restraint member are installed by aligning the replacement winding element's axial passageway with distal end 18a of shaft 18 and pushing the replacement winding element onto shaft 18.

In addition to stretcher 44, the patient restraint may be used in conjunction with any patient support including, for example, a cot, a stretcher, a bed, or a chair, including a stair chair or wheelchair. For example, a suitable stair chair is disclosed in commonly assigned U.S. Pat. No. 6,648,343; a suitable chair is disclosed in commonly assigned U.S. Pat. No. 6,499,163; a suitable cot is disclosed in commonly assigned U.S. Pat. No. 6,125,485; a suitable stretcher is disclosed in commonly assigned U.S. Pat. No. 4,987,623; and a suitable bed is disclosed in commonly assigned U.S. patent application Ser. No. 11/769,959 filed Jun. 28, 2007; all of which are hereby incorporated herein by reference.

Changes and modifications in the specifically described embodiments may be carried out without departing from the principals of the present invention, which is intended to be limited only by the scope of the appended claims, as interpreted according to the principles of patent law.

The embodiments of the invention in which I claim an exclusive property or privilege are defined as follows:

1. A patient retention device comprising:
   a rotatable shaft having an inboard portion and an outboard cantilevered portion;
   a torque-producing device comprising a spring that is operatively connected to said shaft at said inboard portion to rotate said shaft about an axis of rotation; and
   a flexible restraint member coupled to said shaft at said outboard cantilevered portion, wherein said flexible restraint member is selectively windable and unwindable from said outboard cantilevered portion of said shaft.

2. The patient retention device of claim 1, further in combination with a patient support.

3. The patient retention device of claim 2, wherein said patient support comprises one of a stretcher, a bed, a chair, and a cot.

4. The patient retention device of claim 1, wherein said device further comprises a lock mechanism arranged at said shaft to selectively prevent rotation of said shaft.

5. The patient retention device of claim 1, further comprising a cover disposed over said torque-producing device and said inboard portion of said shaft, wherein said outboard cantilevered portion of said shaft is located external to said cover.

6. A method of mounting a flexible restraint member on a patient retention device, said method comprising:
   providing a retractor assembly having a rotatable shaft with an inboard portion and an outboard cantilevered portion;
   providing a torque-producing device comprising a spring that is operatively connected to the inboard portion of the shaft to rotate the shaft about an axis of rotation; and
   removably mounting a flexible restraint member to the shaft at the outboard cantilevered portion, wherein the flexible restraint member is windable and unwindable from the outboard cantilevered portion of the shaft.

7. The method according to claim 6, further comprising:
   providing a frame;
   cantilevering the shaft from the frame;
   rotatably coupling the shaft to the frame;
   winding the flexible restraint member about the shaft; and
   pulling the flexible restraint member to thereby unwind the flexible restraint member from the shaft.

8. The method of claim 7, further comprising:
   providing a housing; and
   positioning the housing over the frame to enclose the torque-producing device.

9. The method of claim 6, further comprising:
   providing a replacement flexible restraint member;
   removing the flexible restraint member from the shaft; and
   placing the replacement flexible restraint member onto the shaft.

10. The method of claim 6, further comprising:
    providing a housing; and
    positioning the housing over the retractor assembly and the torque-producing device with at least a portion of the outboard cantilevered portion of the shaft extending outside the housing.

11. A patient retention device comprising:
    a frame;
    a shaft, said shaft being rotatably mounted to said frame at only one portion of said shaft so as to have a cantilevered portion extending from said frame;
    a flexible restraint member;
    a winding member at said cantilevered portion of said shaft, said winding member adapted to receive said flexible restraint member, and wherein said winding member is non-rotatable relative to said shaft; and
    a torque-producing device comprising a spring that is operatively connected to said shaft.

12. The patient retention device of claim 11, wherein said device further comprises a lock mechanism arranged at said shaft to selectively prevent rotation of said shaft.

13. The patient retention device of claim 11, wherein said winding member is adapted to releasably receive said flexible restraint member.

14. The patient retention device of claim 11, further comprising a cover disposed over said torque-producing device and a portion of said shaft.

15. The patient retention device of claim 11, further in combination with a patient support.

16. A patient retention device comprising:
    a winding member having a first end portion and a second end portion;
    a rotatable shaft having a first end portion and a second end portion, said second end portion adapted to receive said first end portion of said winding member;
    a torque-producing device operatively connected to said first end portion of said shaft to rotate said shaft about an axis of rotation; and
    a flexible restraint member attached to said winding member, wherein said winding member is coupled to said shaft and supported in a cantilever manner so that said winding member projects from said second end portion of said shaft.

17. The patient retention device of claim 16, wherein said second end of said shaft releasably receives said first end of said winding member.

18. The patient retention device of claim 16, wherein said device further comprises a lock mechanism arranged at said shaft to selectively prevent rotation of said shaft.

19. The patient retention device of claim 16, wherein said winding member is adapted to releasably receive said flexible restraint member.

20. The patient retention device of claim 16, further comprising a cover disposed over said torque-producing device and a portion of said shaft.

* * * * *